United States Patent
Li et al.

(10) Patent No.: US 7,908,001 B2
(45) Date of Patent: Mar. 15, 2011

(54) AUTOMATIC MULTI-LEVEL THERAPY BASED ON MORPHOLOGIC ORGANIZATION OF AN ARRHYTHMIA

(75) Inventors: Dan Li, Shoreview, MN (US); Yayun Lin, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 833 days.

(21) Appl. No.: 11/209,976

(22) Filed: Aug. 23, 2005

(65) Prior Publication Data

US 2007/0049974 A1   Mar. 1, 2007

(51) Int. Cl.
*A61N 1/39* (2006.01)
(52) U.S. Cl. .......................................................... 607/4
(58) Field of Classification Search ................ 607/4, 14, 607/15; 600/518
See application file for complete search history.

(56) References Cited

U.S. PATENT DOCUMENTS

| | | | |
|---|---|---|---|
| 4,023,564 A | 5/1977 | Valiquette et al. |
| 4,336,810 A | 6/1982 | Anderson et al. |
| 4,428,378 A | 1/1984 | Anderson et al. |
| 4,550,221 A | 10/1985 | Mabusth |
| 4,686,332 A | 8/1987 | Greanias et al. |
| 4,830,006 A | 5/1989 | Haluska et al. |
| 4,865,036 A | 9/1989 | Chirife |
| 4,872,459 A | 10/1989 | Pless et al. |
| 4,880,005 A | 11/1989 | Pless et al. |
| 5,002,052 A | 3/1991 | Haluska |
| 5,107,850 A | 4/1992 | Olive |
| 5,144,947 A | 9/1992 | Wilson |
| 5,158,092 A | 10/1992 | Glace |
| 5,161,527 A | 11/1992 | Nappholz et al. |
| 5,161,529 A | 11/1992 | Stotts et al. |
| 5,176,137 A | 1/1993 | Erickson et al. |
| 5,181,511 A | 1/1993 | Nickolls et al. |
| 5,193,550 A | 3/1993 | Duffin |
| 5,209,229 A | 5/1993 | Gilli |
| 5,217,021 A | 6/1993 | Steinhaus et al. |
| 5,222,493 A | 6/1993 | Sholder |
| 5,224,475 A | 7/1993 | Berg et al. |
| 5,251,624 A | 10/1993 | Bocek et al. |
| 5,257,621 A | 11/1993 | Bardy et al. |
| 5,312,441 A | 5/1994 | Mader et al. |

(Continued)

FOREIGN PATENT DOCUMENTS

EP   0450943   4/1991

(Continued)

OTHER PUBLICATIONS

U.S. Appl. No. 10/955,831, filed Sep. 30, 2004, Kim et al.

(Continued)

*Primary Examiner* — Mark W Bockelman
*Assistant Examiner* — Roland Dinga
(74) *Attorney, Agent, or Firm* — Hollingsworth & Funk, LLC

(57) ABSTRACT

Methods and systems for selecting tachyarrhythmia therapy based on the morphological organization level of the arrhythmia are described. Morphological organization levels of arrhythmias are associated with cardiac therapies. The morphological organization levels are related to cardiac signal morphologies of the arrhythmias. An arrhythmia episode is detected and the morphological organization level of the arrhythmia episode is determined. A cardiac therapy associated with the morphological organization level of the arrhythmia episode is delivered to treat the arrhythmia. For example, the morphological organization levels may be associated with the cardiac therapies based on one or more of retrospective database analysis, patient therapy tolerance, and physician input. The associations may be static or may be dynamically adjusted based on therapy efficacy.

23 Claims, 8 Drawing Sheets

U.S. PATENT DOCUMENTS

| | | | |
|---|---|---|---|
| 5,312,445 A | 5/1994 | Nappholz et al. | |
| 5,324,310 A | 6/1994 | Greeninger et al. | |
| 5,330,505 A | 7/1994 | Cohen | |
| 5,330,508 A | 7/1994 | Gunderson | |
| 5,342,402 A | 8/1994 | Olson et al. | |
| 5,350,410 A | 9/1994 | Kleks et al. | |
| 5,379,776 A | 1/1995 | Murphy et al. | |
| 5,411,031 A | 5/1995 | Yomtov | |
| 5,425,749 A | 6/1995 | Adams | |
| 5,447,519 A * | 9/1995 | Peterson | 607/5 |
| 5,458,620 A | 10/1995 | Adams et al. | |
| 5,472,453 A | 12/1995 | Alt | |
| 5,513,644 A * | 5/1996 | McClure et al. | 600/521 |
| 5,548,619 A | 8/1996 | Horiike et al. | |
| 5,554,177 A | 9/1996 | Kieval | |
| 5,587,970 A | 12/1996 | Greenwood | |
| 5,662,688 A | 9/1997 | Haefner et al. | |
| 5,683,424 A | 11/1997 | Brown et al. | |
| 5,683,431 A | 11/1997 | Wang | |
| 5,685,315 A * | 11/1997 | McClure et al. | 600/521 |
| 5,725,559 A | 3/1998 | Alt et al. | |
| 5,755,737 A | 5/1998 | Prieve et al. | |
| 5,779,645 A | 7/1998 | Olson et al. | |
| 5,782,888 A | 7/1998 | Sun et al. | |
| 5,817,027 A | 10/1998 | Arand et al. | |
| 5,836,971 A | 11/1998 | Starkweather | |
| 5,844,506 A | 12/1998 | Binstead | |
| 5,846,263 A | 12/1998 | Peterson et al. | |
| 5,855,593 A | 1/1999 | Olson et al. | |
| 5,857,977 A | 1/1999 | Caswell et al. | |
| 5,871,512 A | 2/1999 | Hemming et al. | |
| 5,893,882 A * | 4/1999 | Peterson et al. | 607/14 |
| 5,978,707 A | 11/1999 | Krig et al. | |
| 5,999,854 A | 12/1999 | Deno et al. | |
| 6,064,906 A | 5/2000 | Langberg et al. | |
| 6,076,014 A | 6/2000 | Alt | |
| 6,084,253 A | 7/2000 | Turner, Jr. | |
| 6,101,414 A | 8/2000 | Kroll | |
| 6,128,529 A | 10/2000 | Esler | |
| 6,137,308 A | 10/2000 | Nayak | |
| 6,147,680 A | 11/2000 | Tareev | |
| 6,151,524 A | 11/2000 | Krig et al. | |
| 6,167,308 A | 12/2000 | Degroot | |
| 6,178,350 B1 | 1/2001 | Olson et al. | |
| 6,185,459 B1 | 2/2001 | Mehra et al. | |
| 6,192,273 B1 | 2/2001 | Igel et al. | |
| 6,192,275 B1 | 2/2001 | Zhu et al. | |
| 6,212,428 B1 | 4/2001 | Hsu et al. | |
| 6,221,011 B1 | 4/2001 | Bardy | |
| 6,223,078 B1 | 4/2001 | Marcovecchio | |
| 6,230,055 B1 | 5/2001 | Sun et al. | |
| 6,253,102 B1 | 6/2001 | Hsu et al. | |
| 6,266,554 B1 | 7/2001 | Hsu et al. | |
| 6,270,457 B1 | 8/2001 | Bardy | |
| 6,275,732 B1 | 8/2001 | Hsu et al. | |
| 6,277,072 B1 | 8/2001 | Bardy | |
| 6,280,380 B1 | 8/2001 | Bardy | |
| 6,289,248 B1 | 9/2001 | Conley et al. | |
| 6,308,095 B1 | 10/2001 | Hsu et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,393,316 B1 | 5/2002 | Gillberg et al. | |
| 6,398,728 B1 | 6/2002 | Bardy | |
| 6,400,986 B1 | 6/2002 | Sun | |
| 6,418,340 B1 | 7/2002 | Conley et al. | |
| 6,434,417 B1 | 8/2002 | Lovett | |
| 6,438,407 B1 | 8/2002 | Ousdigian et al. | |
| 6,438,410 B2 | 8/2002 | Hsu et al. | |
| 6,440,066 B1 | 8/2002 | Bardy | |
| 6,445,949 B1 | 9/2002 | Kroll | |
| 6,449,503 B1 | 9/2002 | Hsu | |
| 6,477,422 B1 | 11/2002 | Splett | |
| 6,480,734 B1 | 11/2002 | Zhang et al. | |
| 6,487,443 B2 | 11/2002 | Olson et al. | |
| 6,490,478 B1 * | 12/2002 | Zhang et al. | 600/518 |
| 6,564,106 B2 | 5/2003 | Guck et al. | |
| 6,594,523 B1 | 7/2003 | Levine | |
| 6,611,713 B2 | 8/2003 | Schauerte | |
| 6,631,290 B1 | 10/2003 | Guck et al. | |
| 6,636,764 B1 * | 10/2003 | Fain et al. | 607/5 |
| 6,654,639 B1 | 11/2003 | Lu | |
| 6,684,100 B1 | 1/2004 | Sweeney et al. | |
| 6,708,058 B2 | 3/2004 | Kim et al. | |
| 6,731,982 B1 | 5/2004 | Kroll et al. | |
| 6,766,194 B1 * | 7/2004 | Kroll | 607/9 |
| 6,801,806 B2 | 10/2004 | Sun et al. | |
| 6,882,883 B2 | 4/2005 | Condie et al. | |
| 6,885,890 B2 | 4/2005 | Spinelli et al. | |
| 6,888,538 B2 | 5/2005 | Ely et al. | |
| 6,889,079 B2 | 5/2005 | Bocek et al. | |
| 6,909,916 B2 * | 6/2005 | Spinelli et al. | 607/9 |
| 6,922,585 B2 | 7/2005 | Zhou | |
| 6,993,385 B1 | 1/2006 | Routh | |
| 7,031,764 B2 | 4/2006 | Schwartz et al. | |
| 7,031,771 B2 | 4/2006 | Brown et al. | |
| 7,076,289 B2 | 7/2006 | Sakar et al. | |
| 7,085,599 B2 | 8/2006 | Kim et al. | |
| 7,103,405 B2 | 9/2006 | Sarkar et al. | |
| 7,107,098 B2 | 9/2006 | Sharma et al. | |
| 7,129,935 B2 | 10/2006 | Mackey | |
| 7,130,677 B2 | 10/2006 | Brown et al. | |
| 7,130,678 B2 | 10/2006 | Ritscher et al. | |
| 7,184,815 B2 | 2/2007 | Kim et al. | |
| 7,228,173 B2 | 6/2007 | Cazares | |
| 7,277,747 B2 | 10/2007 | Cazares et al. | |
| 7,330,757 B2 | 2/2008 | Ostroff et al. | |
| 7,477,932 B2 | 1/2009 | Lee | |
| 7,558,623 B2 | 7/2009 | Fischell et al. | |
| 7,706,866 B2 | 4/2010 | Zhang et al. | |
| 7,725,184 B2 | 5/2010 | Cazares | |
| 7,729,762 B2 | 6/2010 | Sun | |
| 2002/0183637 A1 | 12/2002 | Kim et al. | |
| 2003/0120316 A1 * | 6/2003 | Spinelli et al. | 607/14 |
| 2003/0144700 A1 * | 7/2003 | Brown et al. | 607/14 |
| 2003/0191403 A1 | 10/2003 | Zhou et al. | |
| 2004/0093035 A1 * | 5/2004 | Schwartz et al. | 607/5 |
| 2004/0111119 A1 * | 6/2004 | Sarkar et al. | 607/5 |
| 2004/0111120 A1 | 6/2004 | Sakar | |
| 2004/0111121 A1 * | 6/2004 | Brown et al. | 607/5 |
| 2004/0167579 A1 * | 8/2004 | Sharma et al. | 607/14 |
| 2004/0176694 A1 * | 9/2004 | Kim et al. | 600/510 |
| 2005/0131476 A1 | 6/2005 | Kim et al. | |
| 2005/0137485 A1 * | 6/2005 | Cao et al. | 600/510 |
| 2005/0137641 A1 | 6/2005 | Naughton | |
| 2005/0192506 A1 | 9/2005 | Kim et al. | |
| 2005/0288600 A1 | 12/2005 | Zhang et al. | |
| 2006/0069322 A1 | 3/2006 | Zhang et al. | |
| 2006/0074331 A1 | 4/2006 | Kim et al. | |
| 2006/0111747 A1 | 5/2006 | Cazares et al. | |
| 2006/0217621 A1 | 9/2006 | Kim | |
| 2006/0253044 A1 | 11/2006 | Zhang et al. | |
| 2006/0281998 A1 | 12/2006 | Li et al. | |
| 2007/0004997 A1 | 3/2007 | Li et al. | |
| 2007/0049974 A1 | 3/2007 | Li et al. | |
| 2007/0142736 A1 | 6/2007 | Cazares | |

FOREIGN PATENT DOCUMENTS

| | | |
|---|---|---|
| EP | 0547733 | 6/1993 |
| EP | 0709112 | 5/1996 |
| EP | 0801960 | 10/1997 |
| EP | 1267993 | 3/2001 |
| EP | 0360412 | 3/2005 |
| EP | 1112755 | 9/2005 |
| WO | WO9840122 | 9/1998 |
| WO | WO/02/24276 A1 | 3/2002 |
| WO | 03047690 | 6/2003 |
| WO | WO 2006/039694 | 4/2006 |
| WO | WO2006039694 | 4/2006 |

OTHER PUBLICATIONS

M. S. Wathen, M.D. et al. Shock Reduction Using Antitachycardia Pacing for Spontaneous Rapid Ventricular Tachycardia in Patients with Coronary Artery Disease. *Circulation 2001*, vol. 104:796-801. © 2001 American Heart Association, Inc.

Martha Kerr. Shock Rate Cut 70% with ICDs Programmed to First Deliver Antitachycardia Pacing: Results of the PainFREE Rx II Trial. NewsRhythms. MedScape CRM News 2003. www.medscape.com.

Lake et al., *Am. J. Physiol. Regul. Integr. Comp. Physiol.*, 283: R789-97 (2002).

Richman et al., *Am. J. Physiol. Heart Circ. Physiol.*, 278: H2039-49 (2000).

2000, Dubin, Rapid Interpretation of EKG's, 2000, Cover Publishing Company, 6th Edition, p. 334-345.

Office Action Response submitted Jun. 24, 2008 from U.S. Appl. No. 11/089,185, 13 pages.

Office Action Response submitted Apr. 8, 2009 from U.S. Appl. No. 11/089,185, 9 pages.

Office Action dated Jul. 24, 2009 from U.S. Appl. No. 11/089,185, 2 pages.

Office Action Response submitted Aug. 4, 2009 from U.S. Appl. No. 11/089,185, 10 pages.

Office Action dated Jan. 13, 2010 from U.S. Appl. No. 11/089,185, 3 pages.

Office Action Response submitted Jan. 27, 2010 from U.S. Appl. No. 11/089,185, 10 pages.

Office Action dated Mar. 24, 2010 from U.S. Appl. No. 11/089,185, 6 pages.

Office Action Response submitted May 20, 2010 from U.S. Appl. No. 11/089,185, 11 pages.

Notice of Allowance dated Jun. 11, 2010 from U.S. Appl. No. 11/089,185, 4 pages.

Notice of Allowance dated Jul. 22, 2010 from U.S. Appl. No. 11/089,185, 4 pages.

Restriction Requirement dated Dec. 21, 2006 from U.S. Appl. No. 10/955,831, 5 pages.

Response to Restriction Requirement submitted Jan. 22, 2007 from U.S. Appl. No. 10/955,831, 14 pages.

Office Action dated Mar. 5, 2007 from U.S. Appl. No. 10/955,831, 15 pages.

Office Action Response submitted Jul. 5, 2007 to office action dated Mar. 5, 2007 from U.S. Appl. No. 10/955,831, 16 pages.

Office Action dated Oct. 9, 2007 from U.S. Appl. No. 10/955,831, 6 pages.

Office Action Response submitted Dec. 10, 2007 to office action dated Oct. 9, 2007 from U.S. Appl. No. 10/955,831, 15 pages.

Pre-Appeal Brief submitted Feb. 14, 2008 from U.S. Appl. No. 10/955,831, 5 pages.

Pre-Appeal Brief Decision dated Apr. 2, 2008 from U.S. Appl. No. 10/955,831, 2 pages.

Appeal Brief submitted May 1, 2008 from U.S. Appl. No. 10/955,831, 25 pages.

Examiners Answer to Appeal Brief dated Jun. 24, 2008 from U.S. Appl. No. 10/955,831, 6 pages.

Reply Brief submitted Aug. 8, 2008 from U.S. Appl. No. 10/955,831, 8 pages.

Appeal Decision dated Dec. 18, 2009 from U.S. Appl. No. 10/955,831, 11 pages.

Office Action Response with RCE submitted Jul. 12, 2010 from U.S. Appl. No. 10/955,831, 10 pages.

Office Action dated Jul. 18, 2006 from U.S. Appl. No. 10/995,655, 9 pages.

Office Action Response submitted Oct. 23, 2006 from U.S. Appl. No. 10/995,655, 14 pages.

Notice of Allowance dated Jan. 9, 2007 from U.S. Appl. No. 10/995,655, 9 pages.

Office Action dated Sep. 11, 2009 from U.S. Appl. No. 11/807,696, 10 pages.

Office Action dated Nov. 23, 2009 from U.S. Appl. No. 11/807,696, 3 pages.

Office Action Response submitted Dec. 11, 2009 from U.S. Appl. No. 11/807,696, 9 pages.

Notice of Allowance dated Jan. 15, 2010 from U.S. Appl. No. 11/807,696, 7 pages.

Office Action dated Feb. 13, 2007 from U.S. Appl. No. 10/995,704, 9 pages.

Office Action Response submitted May 18, 2007 from U.S. Appl. No. 10/995,704, 17 pages.

Office Action dated Aug. 23, 2007 from U.S. Appl. No. 10/995,704, 8 pages.

Office Action Response submitted Oct. 25, 2007 from U.S. Appl. No. 10/995,704, 12 pages.

Office Action dated Nov. 20, 2007 from U.S. Appl. No. 10/995,704, 3 pages.

Pre-Appeal Brief submitted Jan. 28, 2008 from U.S. Appl. No. 10/995,704, 6 pages.

Appeal Brief submitted Apr. 25, 2008 from U.S. Appl. No. 10/995,704, 30 pages.

Examiner's Answer dated Jul. 25, 2008 from U.S. Appl. No. 10/995,704, 8 pages.

Reply Brief submitted Sep. 25, 2008 from U.S. Appl. No. 10/995,704, 10 pages.

Appeal Decision dated Sep. 8, 2010 from U.S. Appl. No. 10/995,704, 6 pages.

Office Action dated Jan. 29, 2009 from U.S. Appl. No. 11/312,279, 9 pages.

Office Action dated Apr. 9, 2009 from U.S. Appl. No. 11/312,279, 2 pages.

Office Action Response submitted Apr. 28, 2009 from U.S. Appl. No. 11/312,279, 10 pages.

Office Action dated Aug. 19, 2009 from U.S. Appl. No. 11/312,279, 13 pages.

Office Action Response submitted Jan. 14, 2010 from U.S. Appl. No. 11/312,279, 14 pages.

Office Action dated May 1, 2008 from U.S. Appl. No. 11/267,071, 7 pages.

Office Action dated Sep. 24, 2008 from U.S. Appl. No. 11/267,071, 2 pages.

Office Action Response submitted Oct. 23, 2008 from U.S. Appl. No. 11/267,071, 13 pages.

Office Action dated Jan. 16, 2009 from U.S. Appl. No. 11/267,071, 8 pages.

Office Action Response submitted Apr. 15, 2009 from U.S. Appl. No. 11/267,071, 9 pages.

Office Action dated Jun. 12, 2009 from U.S. Appl. No. 11/267,071, 5 pages.

Office Action Response submitted Sep. 10, 2009 from U.S. Appl. No. 11/267,071, 10 pages.

Notice of Allowance dated Dec. 17, 2009 from U.S. Appl. No. 11/267,071, 4 pages.

International Preliminary Report on Patentability from International Application No. PCT/US2006/047215 dated Jul. 3, 2008, 8 pages.

International Search Report and Written Opinion from International Application No. PCT/US2006/047215 dated Jun. 19, 2007, 13 pages.

International Preliminary Report on Patentability from International Application No. PCT/US2006/032872 dated Mar. 6, 2008, 6 pages.

International Search Report and Written Opinion from International Application No. PCT/US2006/032872 dated Feb. 12, 2007, 8 pages.

Invitation to Pay Additional Fees from International Application No. PCT/US2005/035641 dated Jan. 3, 2006, 8 pages.

International Search Report and Written Opinion from International Application No. PCT/US2005/035641 dated Jun. 12, 2006, 20 pages.

International Preliminary Report on Patentability from International Application No. PCT/US2005/035641 dated Apr. 12, 2007, 9 pages.

Office Action dated Jun. 16, 2009 from European Application No. 05800765.9, 3 pages.

Office Action Response dated Dec. 15, 2009 from European Application No. 05800765.9, 39 pages.

U.S. Appl. No. 11/151,102, filed Dec. 14, 2006, Li.

U.S. Appl. No. 11/038,996, filed Jul. 20, 2008, Li.

U.S. Appl. No. 11/312,280, filed Jun. 21, 2007, Cazares et al.

U.S. Appl. No. 11/312,219, filed Dec. 20, 2005, Cazares et al.

U.S. Appl. No. 10/995,655, filed Nov. 23, 2004, Cazares.

U.S. Appl. No. 10/995,704, filed Nov. 23, 2005, Cazares et al.

U.S. Appl. No. 11/089,185, filed Mar. 24, 2005, Kim et al.

"Vitality 2 Implantable Cardioverter Defibrillator System Guide", Guidant Corporation, 2004, Cover pages and pp. 3-15 to 3-19.

Gold, Michael R., et al., "Advanced Rhythm Discrimination for Implantable Cardioverter Defibrillators Using Electrogram Vector Timing and Correlation", *Journal of Cardiovascular Electrophysiology*, vol. 13, No. 11, Nov. 2002, pp. 1092-1097.

Mercando et al., *Measurement of Differences in Timing and Sequence Between Two Ventricular Electrodes as a Means of Tachycardia Differentiation*, PACE, Part II, vol. 9, Nov.-Dec. 1986, 1069-1078. (abstract only).

Office Action from U.S. Appl. No. 11/089,185 dated Nov. 3, 2009, 9 pages.

Office Action from U.S. Appl. No. 11/089,185 dated May 15, 2009, 11 pages.

Office Action from U.S. Appl. No. 11/089,185 dated Dec. 8, 2008, 8 pages.

Office Action from U.S. Appl. No. 11/089,185 dated Mar. 28, 2008, 14 pages.

\* cited by examiner

AUTOMATIC MULTI-LEVEL THERAPY BASED ON MORPHOLOGIC ORGANIZATION OF AN ARRHYTHMIA

FIELD OF THE INVENTION

The present invention relates generally to cardiac therapy devices and methods, and, more particularly, to automatic selection of tachyarrhythmia therapies based on morphological organization of the tachyarrhythmia.

BACKGROUND OF THE INVENTION

Proper cardiac function relies on the synchronized contractions of the heart at regular intervals. When the heart is functioning normally, synchronized cardiac contractions are initiated at the sinoatrial node and the heart is said to be operating in normal sinus rhythm. However, if contractions of the heart become irregular or uncoordinated, or if the contraction rate is too fast or too slow, the heart rhythm is described as arrhythmic. Cardiac arrhythmia may be caused, for example, by disease processes or from aberrant electrical conduction patterns occurring in the heart tissue. Cardiac arrhythmia impairs cardiac pumping efficiency and some types of cardiac arrhythmia can be life threatening.

A cardiac arrhythmia that originates in an atrial region of the heart is denoted a supra-ventricular tachyarrhythmia (SVT). Atrial fibrillation and atrial flutter are examples of SVT. Both conditions are characterized by rapid, uncoordinated contractions of the atria resulting in hemodynamically inefficient pumping action.

Another example of SVT is sinus tachycardia, which is an increased heart rate due to exercise or a quick emotional response. In contrast to atrial fibrillation and atrial flutter, sinus tachycardia is characterized by rapid, coordinated contractions of the atria resulting in hemodynamically efficient pumping action, compensating for the increased strain placed upon the body during exercise or quick emotional responses. Whereas atrial fibrillation and atrial flutter are "abnormal" (yet not lethal), sinus tachycardia is "normal" (and also not lethal).

Cardiac arrhythmias originating in a ventricular region of the heart are denoted ventricular tachyarrhythmias. Ventricular tachycardia (VT) is characterized by rapid ventricular contractions and can degenerate into ventricular fibrillation (VF). Ventricular fibrillation produces extremely rapid, non-coordinated contractions of the ventricles. Ventricular fibrillation is fatal unless the heart is returned to sinus rhythm within a few minutes.

Implantable cardiac rhythm management (CRM) devices, including pacemakers and implantable cardioverter/defibrillators, and have been used to deliver effective treatment to patients with serious cardiac arrhythmias. Cardiac rhythm management devices may treat cardiac arrhythmias with a variety of tiered therapies. These tiered therapies range from delivering low energy pacing pulses timed to assist the heart in maintaining pumping efficiency to providing high-energy shocks to treat and/or terminate fibrillation. To effectively deliver these treatments, the CRM device must first identify the type of arrhythmia that is occurring, after which appropriate therapy may be delivered to the heart.

SUMMARY OF THE INVENTION

The present invention is directed to methods and systems for selecting tachyarrhythmia therapy based on the morphological organization level of the arrhythmia. One embodiment of the invention involves a method for delivering cardiac therapy. Morphological organization levels of arrhythmias are associated with cardiac therapies. The morphological organization levels are related to cardiac signal morphologies of the arrhythmias. An arrhythmia episode is detected and the morphological organization level of the arrhythmia episode is determined. A cardiac therapy associated with the morphological organization level of the arrhythmia episode is delivered to treat the arrhythmia. For example, the morphological organization levels may be associated with the cardiac therapies based on one or more of retrospective database analysis, patient therapy tolerance, and physician input.

The cardiac therapy delivered may be a multi-level therapy that includes a number of therapy components, such as one or more anti-tachycardia pacing components and/or one or more shock therapy components. After one or more therapy component is delivered, the method may include sensing for redetection of the arrhythmia following delivery of one or more of the therapy components. Sensing for redetection may occur more often for a more organized arrhythmia episode and less often for a less organized arrhythmia episode.

In one implementation, associating the morphological organization levels with the cardiac therapies involves associating the morphological organization levels with therapy wander times. The therapy wander times represent lengths of time that the cardiac therapies are delivered.

The morphological organization level of the arrhythmia episode may be determined based on one or more of morphological regularity of a cardiac electrogram signal of the arrhythmia episode, entropy of the cardiac electrogram, and hemodynamic stability of the arrhythmia episode.

According to one aspect of the invention, the morphological organization level of the arrhythmia episode is determined by comparing morphologies of one or more of the cardiac beat signals of the arrhythmia episode to a template. Alternatively, or additionally, the morphological organization level of the arrhythmia episode may be determined by comparing a morphology of a cardiac beat signal of the arrhythmia episode to a morphology of another cardiac beat signal of the arrhythmia episode.

The morphological organization level of the arrhythmia episode may be determined based on rate irregularity of the arrhythmia episode, the morphological complexity of a cardiac electrogram signal of the arrhythmia episode, and/or the hemodynamic stability of the arrhythmia episode. For example, determining the morphological organization may involve using one or more thresholds respectively associated with one or more measures of morphological organization delivering the cardiac therapy associated with the morphological organization level of the arrhythmia episode comprises:

Associating the morphological organization levels with the cardiac therapies may involve statically or dynamically associating the morphological organization levels with the cardiac therapies. According to one aspect of the invention, the morphological organization levels may be associated with the cardiac therapies based on one or more of historical data, patient therapy tolerance and physician input. After an initial association is made, the associations between the morphological organization levels and the therapies may be dynamically changed based on efficacy of the cardiac therapies.

Another embodiment of the invention is directed to a cardiac rhythm management device. The cardiac rhythm management device includes a processor that is configured to associate the morphological organization levels of arrhythmias with cardiac therapies. The processor is also configured to determine a morphological organization level of an arrhythmia episode based on cardiac signals. An arrhythmia detector is configured to detect the arrhythmia episode and therapy circuitry delivers a cardiac therapy associated with the morphological organization level of the arrhythmia episode. The cardiac rhythm management device typically includes a memory which may be used to store a library of the cardiac therapies and an association map between the morphological organization levels and the cardiac therapies. According to one aspect of the invention, the cardiac rhythm management device is patient implantable.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
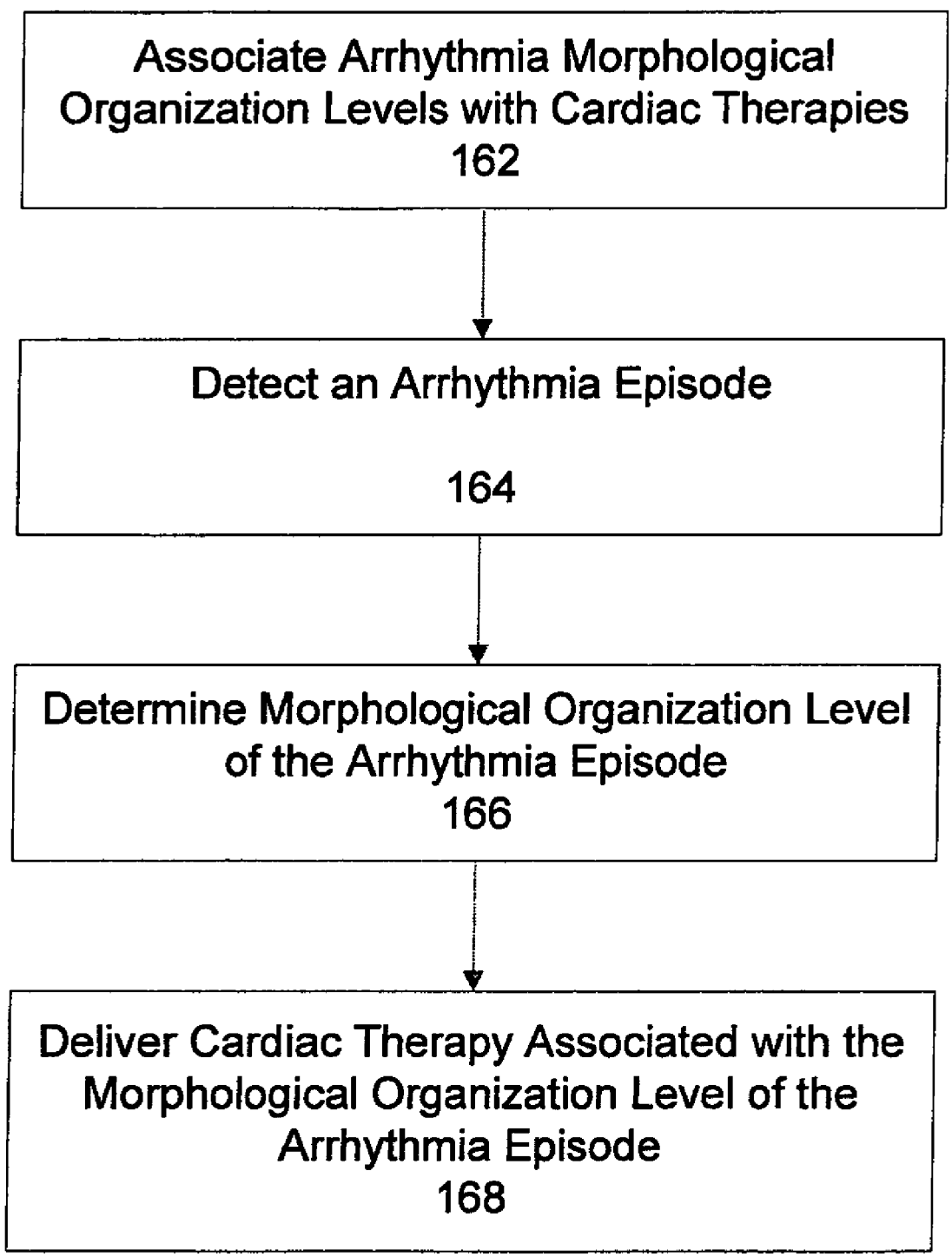
FIG. 1 is a flowchart illustrating a method of delivering multi-level therapy based on morphological organization of an arrhythmia in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Ventricular tachyarrhythmias are fast heart rhythms that arise within one or more ventricles. Atrial tachyarrhythmias, e.g., atrial flutter or atrial fibrillation, are fast heart rhythms that arise within one or more atria. Electrogram (EGM) or electrocardiogram (ECG) signals representative of ventricular or atrial tachyarrhythmic beats may exhibit a number of different morphology patterns. Some types of tachyarrhythmia may exhibit a generally monomorphic pattern. Electrogram signals representing a monomorphic tachyarrhythmia may have a fairly regular rhythm and a similar shape or morphology.

Other types of tachyarrhythmia may comprise multi-morphology or polymorphic tachyarrhythmia. Each beat of a multi-morphology or polymorphic tachyarrhythmia may be different. Ventricular fibrillation is an example of a polymorphic ventricular tachyarrhythmia that presents a disorganized, inconsistent morphology.

Episodes of tachyarrhythmia may last only a few beats and may produce minimal symptoms. If the cardiac rate is relatively low, the tachyarrhythmia may be tolerated even if sustained for a number of minutes. Tachyarrhythmia may be treated using a variety of therapies. For example, in some cases, ventricular tachycardia (VT) may be effectively treated by pacing at relatively high energy output when compared to bradycardia pacing. Pacing to mitigate VT may involve one or more pacing bursts and is typically denoted anti-tachycardia pacing (ATP). Other types of VT may require a more aggressive therapy, including low energy cardioversion shocks and/ or high energy defibrillation shocks. Still other types of VT may terminate spontaneously without therapy or may not require therapy.

The most dangerous form of polymorphic ventricular tachyarrhythmia is denoted ventricular fibrillation, which involves very rapid, small-scale, and uncoordinated contractions. The rapid contractions cause a precipitous drop in blood pressure and compromised hemodynamic output. Ventricular fibrillation involving heart rates in excess of about 220 beats per minute rarely terminate spontaneously and may be fatal without rapid therapeutic intervention.

The present invention is directed to methods and systems for automatically delivering multi-level arrhythmia therapy selected to treat the particular arrhythmia type based on the morphological organization of the cardiac signals of the arrhythmia episode. The morphological organization of the arrhythmia may be determined, for example, by directly evaluating the morphological organization of the cardiac electrical signal, e.g., electrocardiogram (ECG) or electrogram (EGM), or by evaluating variations of features extracted from other cardiac signals, such as hemodynamic sensor signals. The method involves classifying ventricular or atrial arrhythmia episodes according to morphological organization level, and delivering multi-level tachyarrhythmia therapy associated with the morphological organization level of the arrhythmia episode. In various implementations, arrhythmias may be classified based on one or more measures of morphological organization of the electrogram signal, including morphological regularity of the cardiac beats (similarity in the morphology of cardiac beat signals of the arrhythmia), entropy or complexity analysis (measure of the randomness of the electrogram signal of the arrhythmia), hemodynamic status (e.g., as measured by impedance. oxygen saturation, heart sound, activity and/or pressure sensors), and/or by other measures. Arrhythmia rate information may also be used in addition to one or more morphological organization measures.

Each arrhythmia morphological organization level is associated with a distinct cardiac therapy scheme (RxS). The cardiac therapy scheme may involve a tiered therapy approach wherein one or more therapy components of the therapy scheme provide an increasingly aggressive therapy to the patient.

FIG. 1 is a flowchart illustrating a method of providing multi-level tachyarrhythmia therapy in accordance with embodiments of the invention. The method involves associating 110 arrhythmia morphological organization levels with cardiac therapies. The cardiac therapies may include one or more component therapies that are delivered sequentially, for example. The association between cardiac therapies and arrhythmia morphological organization level may be initially based on analysis of historical data pertaining to the success or failure of various therapy schemes to convert different types of arrhythmia. The mapping of associations between therapies and morphological organization level may be performed automatically by the CRM device or manually by a physician or other person communicating with the CRM through a programmer, for example.

If an arrhythmia episode is detected 120, e.g., by examination of rate and/or morphology analysis, the morphological organization level of the arrhythmia is determined 130. The cardiac therapy associated with the morphological organization level is delivered 140.

A general rule of programming different levels of antitachycardia therapy is that the aggressiveness of the therapy is proportional to the severity of the arrhythmia. Different combinations of ATP and/or shock therapy components can be programmed for different levels of arrhythmia morphological organization levels. For example, for a more organized arrhythmia, a cardiac therapy can be programmed as the following sequence of therapy components: ATP1→ATP2→APT3→Cardioversion→Shock. For a more severe, more disorganized arrhythmia, the cardiac therapy sequence can be programmed as ATP1→Cardioversion→Shock. For a very severe, very disorganized arrhythmia, the cardiac therapy sequence can be programmed as Cardioversion→Shock. Cardioversions and shocks with different energies can be used to make the cardiac therapy complete and practical. In the above examples, ATP1 and ATP2 may be ATPs with different parameters settings. For example, ATP2 may have more pacing bursts and/or shorter pulse duration and/or higher pacing energy than ATP1.

In some implementations, arrhythmia redetection may be enabled between two components of the cardiac therapy scheme. For example, arrhythmia redetection may be performed between the ATP1 and ATP2 components and/or the ATP2 and ATP3 components and/or the ATP3 and Cardioversion components and/or the Cardioversion and Shock components of the first cardiac therapy sequence example above. In some embodiments, the redetected arrhythmia may be analyzed for determination of the morphological organization of the redetected arrhythmia. The cardiac therapy delivered to treat the initially detected arrhythmia may be modified so that a cardiac therapy associated with the morphological organizational level of the redetected arrhythmia is delivered to the patient.

Sequences of therapy components of a programmed cardiac therapy may include more ATP components and more redetection periods for arrhythmias that are more organized when compared to the number of ATP components and redetection periods for arrhythmias that are less organized. A more organized arrhythmia is more likely to be converted by ATP therapy. Even if one ATP attempt fails to convert the arrhythmia, an additional attempt or attempts may succeed. Therefore, a cardiac therapy delivered to treat a more organized arrhythmia may include a number of ATP components. The device may enable redetection periods between two or more of the ATP components to check if the therapy has converted the arrhythmia. If the arrhythmia has been converted, the device does not deliver additional components of the programmed therapy.

In contrast, ATP is less likely to be effective if an arrhythmia is or becomes less organized. Therefore, fewer ATP components are used prior to delivering a shock to convert arrhythmias that are highly disorganized. The use of fewer ATP therapy components reduces the number of redetection periods that are enabled during the therapy delivery.

Figure 2:
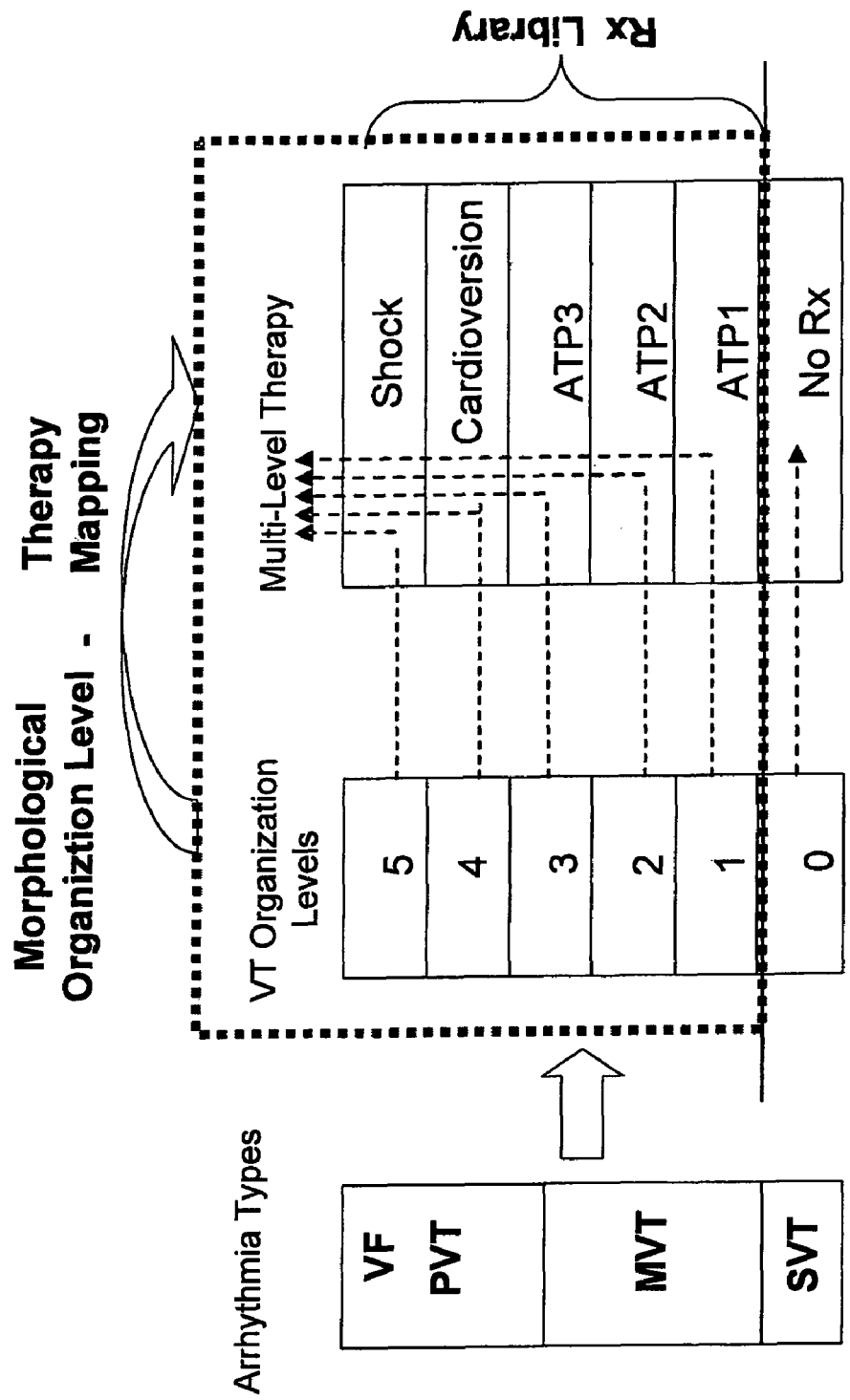
FIG. 2 is a diagram illustrating the concept of mapping associations between morphological organization level and arrhythmia therapy in accordance with embodiments of the invention.

The diagram of FIG. 2 illustrates the concept of mapping associations between morphological organization level and arrhythmia therapy in accordance with embodiments of the invention. FIG. 2 depicts various arrhythmia types, including for example, ventricular fibrillation (VF), polymorphic ventricular tachyarrhythmia (PVT), monomorphic ventricular tachyarrhythmia (MVT), and superventricular tachyarrhythmia (SVT). Each of these arrhythmia types corresponds to one or more morphological organization levels. In this example, the morphological organization levels are numbered 0-5 with 0 representing the most organized arrhythmia, in this case, SVT, and 5 representing the most disorganized arrhythmia, e.g., VF. More or fewer morphological organization levels may be used.

The use of additional organization levels provides therapy delivery that is more finely tuned to the particular morphological organization level of the arrhythmia. In some implementations, the arrhythmia morphological organization level may be expressed as a continuous value. Therapy parameters, e.g., therapy times, therapy energies, therapy attempts, may be adjusted based on the value of the morphological organization level for the particular arrhythmia.

Each morphological organization level is associated with a cardiac therapy that may include multiple therapy components, e.g., ATP, cardioversion, or shock components. Parameters of the various cardiac therapies and/or therapy components are stored in memory in a therapy library (Rx library). In the particular example illustrated in FIG. 2, the cardiac therapy for each morphological organization level is dependent on the cardiac therapy of the previous level. In this example, each cardiac therapy adds a new therapy component as the morphological organization level increases, e.g., level 1 is associated with ATP1, level 2 is associated with APT1→ATP2, level 3 is associated with ATP1→ATP2→ATP3, and so forth. In other implementations, the cardiac therapy for each morphological level may be programmed to be independent of the cardiac therapy of the previous morphological organization level. For example, the cardiac therapy associated with level 4 may involve ATP2→Cardioversion→Shock, and the cardiac therapy associated with level 5 may only include the Shock components. The therapy components may be programmed to be delivered in any combination and/or in any order that effectively treats the arrhythmia having the associated morphological organization level.

In various implementations, the length of time that a therapy component is attempted and/or the number of therapy components that are attempted may be programmed as a function of the morphological organization level. For each morphological organization level, the associated cardiac therapy may involve a sequence of therapy components queued in order of aggressiveness or effectiveness. In such a scenario a "wander time" is associated with each morphological organization level. Specifically, therapy to treat a less severe (more organized) arrhythmia may involve a longer wander time through the therapy library than the therapy to treat a more severe (less organized) arrhythmia. For example, the longer wander time through the therapy library may result in more ATP therapy components delivered to convert the arrhythmia. As illustrated in FIG. 2, therapy to treat a level 1 arrhythmia includes three ATP therapy components as compared to therapy to treat a level 3 arrhythmia which includes only one ATP therapy component.

Additionally, or alternatively, the length of time that a therapy component or a sequence of therapy components are attempted may be a function of the morphological organization level. For example, if the morphological organization level is relatively low, corresponding to a more organized arrhythmia, then an ATP therapy component may be delivered for a longer period of time before a shock is delivered as compared to the period of time that an ATP therapy component is delivered for a less organized arrhythmia. i.e., an arrhythmia having a higher morphological organization level. A time out for one or a sequence of ATP therapy components prior to delivering a more aggressive or the most aggressive therapy may be longer from a more organized arrhythmia than for a less organized arrhythmia. For example, one more parameters of the cardiac therapy may be dependent on the morphological organization level which may be expressed as a continuous variable. For example, the CRM device may be programmed to deliver the therapy component sequence ATP2→ATP3 for a period of time proportional to the morphological organization level. If the arrhythmia is not converted after the period of time, a more aggressive therapy is delivered, such as a shock.

Parameters of the cardiac therapy and/or therapy components, and/or mapping between morphological organization levels and cardiac therapies may be static, meaning that for a particular patient, the cardiac therapy for each morphological organization level is time-invariant after it is set, e.g., initially established in the device or set via the device programmer. In one implementation, the therapy/therapy component parameters and associations between the morphological organization levels and the cardiac therapies are made by the patient's physician communicating with a CRM device via a programmer. A user interface program running on the programmer may step the physician through a series of dialog boxes or prompts that allow the physician to set up the therapy/therapy component parameters and the organization level to therapy mapping. In other implementations, the associations may be initially mapped in the device to default values determined based at least in part on clinical observations and may involve global optimization of clinical data. The default therapy parameters and/or mapping associations may take into account patient indications to develop a more efficient therapy map. Once made and stored in the memory of the device, the therapy associations may remain static until manually changed, e.g., changed by the physician.

In other embodiments, cardiac therapy parameters and/or mapping between morphological organization levels and cardiac therapies may be dynamic. The therapy/therapy component parameters and/or organization level to therapy associations may be initially determined as in the static case presented above and stored in the device memory. Following or during therapy delivery by the device to treat an arrhythmia episode, the efficacy of the therapy may be evaluated based on therapy efficacy. The cardiac therapy parameters and/or mapping associations may be modified based on the evaluation of therapy efficacy. For example, if the therapy is excessively aggressive for the particular morphological organization level, the therapy parameters of the therapy components may be changed, or different, less aggressive, therapy components may be mapped to the morphological organization level. If the therapy is not sufficiently aggressive to convert the arrhythmia in a timely fashion, the therapy parameters and/or the morphological organization level to therapy mapping may be modified so that a more aggressive therapy is delivered. Various methods and systems for delivering adaptive tachyarrhythmia therapy based on historical success, aspects of which may be utilized in the embodiments presented herein, is described in commonly owned U.S. Pat. No. 6,801,806 which is incorporated herein by reference.

In some embodiments, the device may include circuitry for performing processes of dynamic modification for setting cardiac therapy parameters and/or mapping associations between morphological organization levels and cardiac therapies. Dynamic modification of the cardiac therapy parameters and/or the mapping between organization levels and therapies may be performed during and/or after an arrhythmia episode. In some scenarios, the device may automatically change parameters and mapping during therapy in an attempt to convert an occurring arrhythmia episode. In some scenarios, the modification of the therapy parameters and/or mapping may be retrospectively applied following conversion of an arrhythmia to a normal rhythm. For example, the device may evaluate the effectiveness of the therapy sequence after the arrhythmia terminates to determine if or how the therapy parameters and/or mapping would best be modified.

Figure 3:
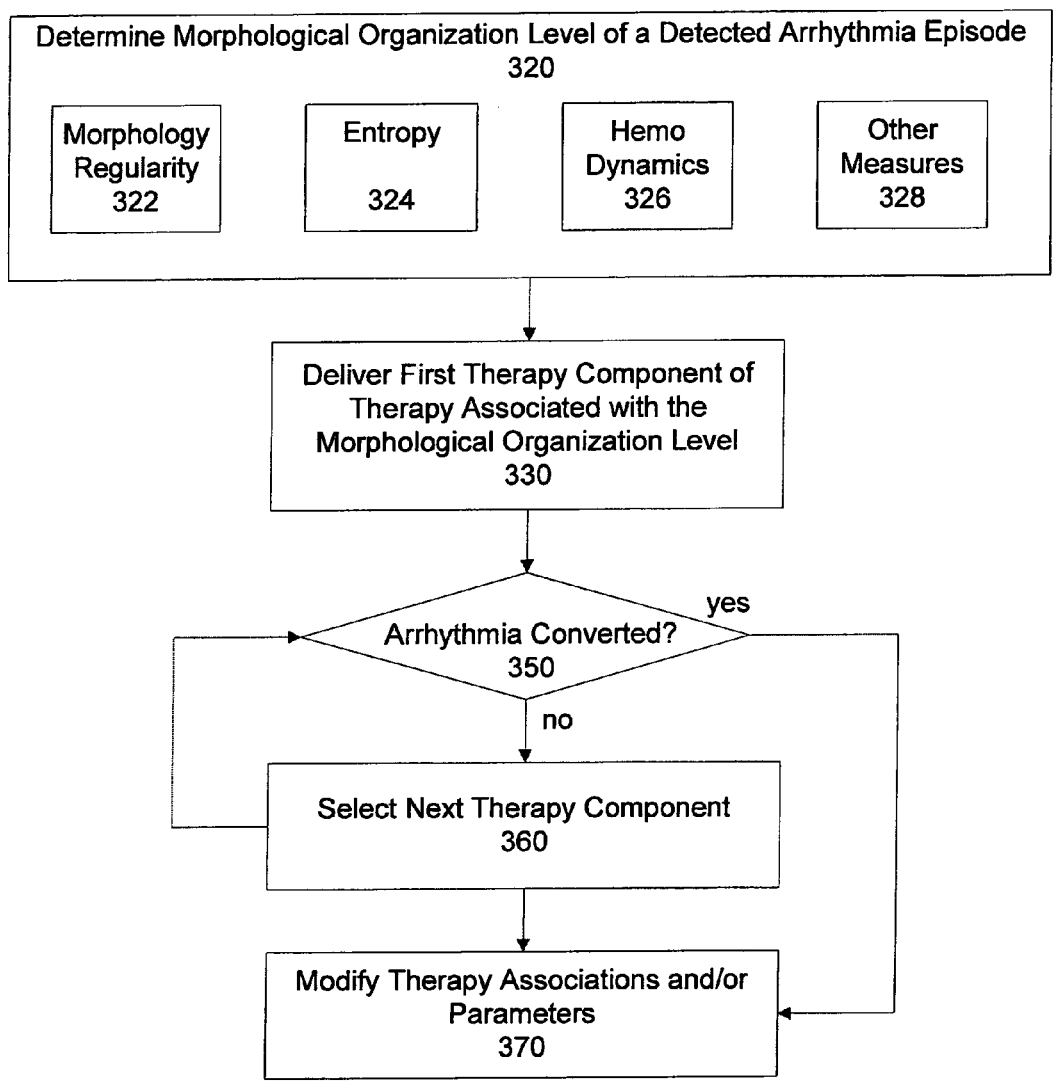
FIG. 3 is a flowchart illustrating a process for dynamic modification of a multi-level therapy in accordance with embodiments of the invention.

The flowchart of FIG. 3 illustrates a process for dynamic modification of the multi-level therapy described in connection with FIG. 2. Morphological organization levels may be initially associated with cardiac therapies based on physician input and/or default values as previously discussed. Initial cardiac therapy/therapy component parameters, including therapy component sequences, time out intervals, wander time, burst rates, pace and/or shock energy levels, and/or other parameters may be initially set.

If an arrhythmia episode is detected, the morphological organization level of the arrhythmia is determined 320. Before or during determination of the morphological organization level, the arrhythmia may be classified as an arrhythmia that does not require treatment. In the example provided in FIG. 2, ventricular tachyarrhythmias are divided into five levels of morphological organization. Arrhythmias that are atrial in origin (SVTs) are classified as having a morphological organization level of zero which is associated with no therapy delivery. The initial classification of an arrhythmia as VT or SVT may be performed by any interval-based or morphology-based technique.

The morphological organization of the arrhythmia episode may be assessed using a one or a combination of techniques. For example, morphological organization may be assessed by analyzing the sensed cardiac electrogram signal of the arrhythmia episode. Analysis of the electrogram signal may involve determining the morphological regularity 322 of the electrogram signal beats. In other implementations, the morphological organization level may be assessed based on the entropy 324 associated with the electrogram signal, or other measures of data distributions. Hemodynamic stability 326 is correlated to morphological stability of the electrogram signal and may be used to determine the morphological organization level. Other measures 328 of determining the morphological organization level of the electrogram may alternatively or additionally be used.

In some embodiments, a single one of the techniques described above may be implemented to determine the morphological organization level of the arrhythmia episode. In other embodiments, a combination of techniques may be used. If a multiple techniques are used, then the morphological organization level of the arrhythmia episode may be determined by combining the results of the techniques by any data fusion method, such as majority voting, or weighted average, for example.

Following determination of the morphological organization level, the first therapy component of the therapy scheme associated with the organization level is delivered 330. A period of redetection may follow delivery of therapy component. If the arrhythmia is converted 350, then the therapy parameters and/or associations may be modified 370. If the arrhythmia is not converted 350, then additional therapy components of the therapy scheme are applied.

Modification of the therapy parameters and/or associations may be based on the success or failure of the therapy to convert the arrhythmia. For example, if the therapy failed to convert the arrhythmia, then the morphological organization level/therapy association may be changed so that the morphological organization level is associated with a more aggressive therapy. On the other hand, if the therapy was highly successful at converting the arrhythmia, e.g., if the arrhythmia was converted by the first component of the therapy, the morphological organization level/therapy association may be remapped so that the morphological organization level is associated with a less aggressive therapy. In the case of a highly successful therapy, remapping the organization level/therapy association to provide a less aggressive therapy may be attempted to increase device lifetime and enhance patient comfort. In addition to modification of the morphological organization level/therapy associations, one or more of the therapy parameters, e.g., burst rate, stimulation energy, delivery time of one or more therapy components, and the like, may also be modified.

Figure 4A:
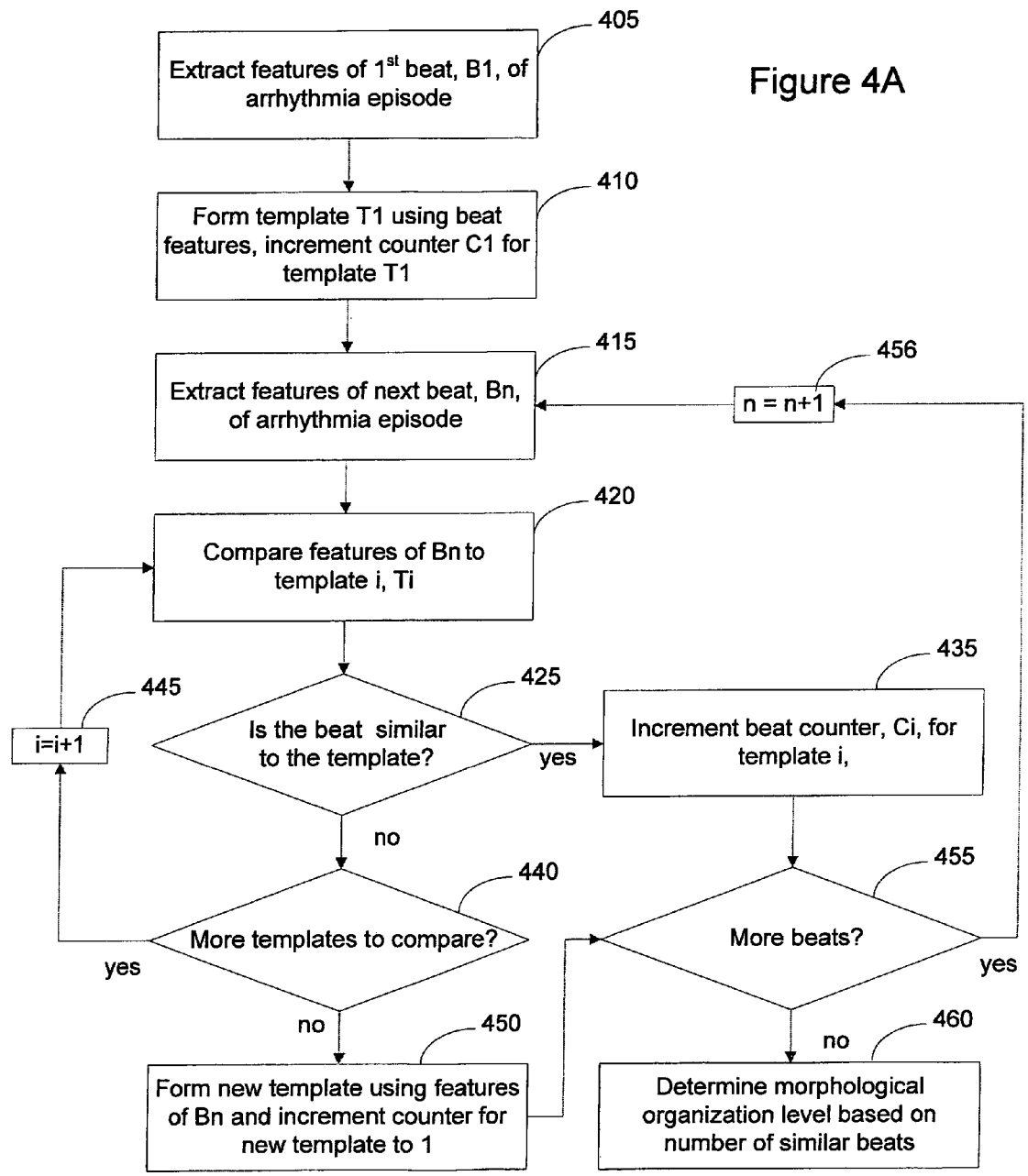
FIG. 4A depicts a method for determining the number of morphologically similar beats in an arrhythmia episode in accordance with embodiments of the invention.
Figure 4B:
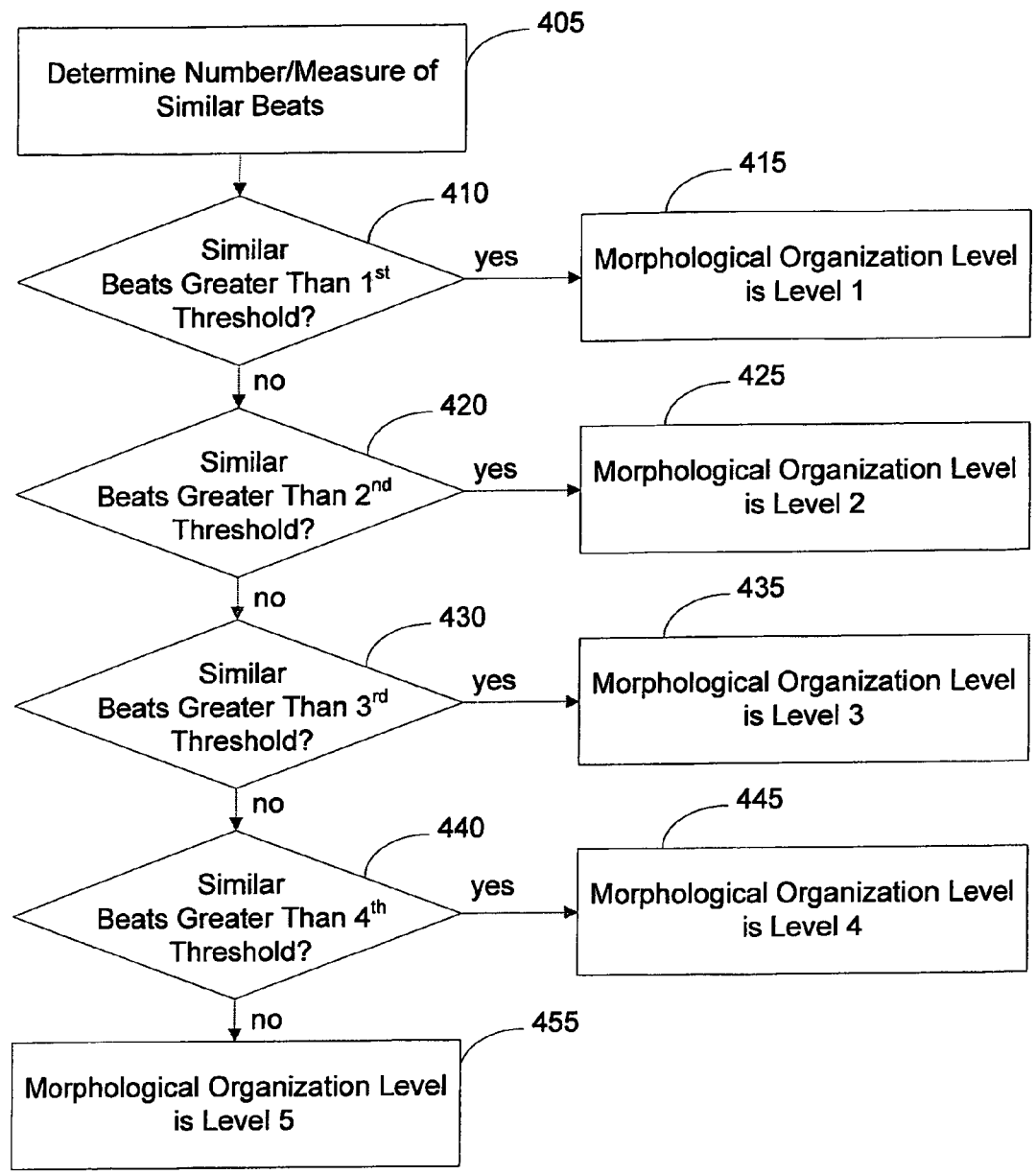
FIG. 4B illustrates a process of determining the morphological organization level based on the number of similar beats of an arrhythmia episode in accordance with embodiments of the invention.

As discussed in connection with element 320 of FIG. 3, various processes may be implemented to determine the morphological organization level of the arrhythmia episode. In one implementation, the morphological regularity 322 of the electrogram signal may be determined based on the number of similar beats in an arrhythmia episode. This implementation is illustrated by the flowchart of FIGS. 4A and 4B. The number of similar beats in the arrhythmia episode is compared to thresholds associated with each morphological organization level.

FIG. 4A depicts a method for determining the number of similar beats in an arrhythmia episode. One or more features of a 1$^{st}$ arrhythmia episode beat, denoted B1, are extracted 405. The extracted features of B1 are used to form 410 a cardiac template. Cardiac templates may include representative waveforms and/or information derived from waveforms, such as various attributes and/or ranges of attributes of the sensed cardiac signal, including, but not limited to: timing and/or rate information, QRS width, T-wave amplitude, Q-wave amplitude, QT interval, R-R intervals, interval statistics, or other intervals or attributes useful for determining a correspondence between a cardiac waveform and a template. In this particular example, a cardiac waveform template is formed by identifying one or more cardiac waveform features representative of a particular cardiac beat morphology. The particular waveform features may include morphological features such as critical points, significant points, curvature, local extrema, inflection points, rise or fall times, slopes, areas above and/or below baselines, and frequency and/or wavelet coefficients, or the like.

A next beat, Bn, is detected and features extracted 415. The features of Bn are compared 420 to the template formed from the first beat to determine the similarity of the Bn features to the template features. For example, the similarity of the beat to the template may be expressed in terms of a feature correlation coefficient (FCC). Methods and systems for determining similarity between episode beats and cardiac template beats based on calculating correlation coefficients are described in commonly owned U.S. Publication No. 2006/0074331 and incorporated herein be reference. Similarity between a beat and a template may be confirmed, for example, if the FCC is greater then a predetermined number, e.g., about 0.9.

If the Bn is similar 425 to the template, then the counter for the template is incremented 435 If Bn is not similar 425 to the template, T1, then another template is formed 450 based on the features of Bn. The process continues as in blocks 415-455 by comparing additional episode beats 445, 420 with previously formed templates 440 and forming 450 new templates if the beats are not similar to any of the previously formed templates. Each time a beat is similar to a template, the counter for the template is incremented. If any beat matches an existing template, then the counter for that template is incremented 435. After all, a sufficient number, or a representative sample of beats from the arrhythmia episode are evaluated 455, 456, the morphological organization level may be determined 460 based on the counter values and/or the number of templates formed, for example.

FIG. 4B illustrates a process of determining the morphological organization level based on the number of similar beats of an arrhythmia episode in accordance with embodiments of the invention. This process relies on multiple thresholds, corresponding to a threshold measure of similar beats for each morphological organization level. The thresholds may be expressed, for example, as a percentage of beats, or as a predetermined number of beats, e.g., x out of y beats, or as a number of distinct templates created, or in any other convenient form.

The highest counter value resulting from the process described in connection with FIG. 4A represents the largest number of similar beats in the arrhythmia episode. This value may be converted, for example, to a percentage or other measure. The measure of similar beats is determined 405 and is compared 410, 420, 430, 440 to a threshold for each morphological organization level. If the measure of similar beats is consistent with the threshold for a particular morphological organization level, then the arrhythmia episode is classified 415, 425, 435, 445, 455 as having that morphological organization level. Highly organized arrhythmias corresponding in this example to a morphological organization level of 1, have the highest number or percentage of similar beats. The most disorganized arrhythmias, corresponding in this example to morphological organization level 5, have the least number or percentage of similar beats.

Figure 5:
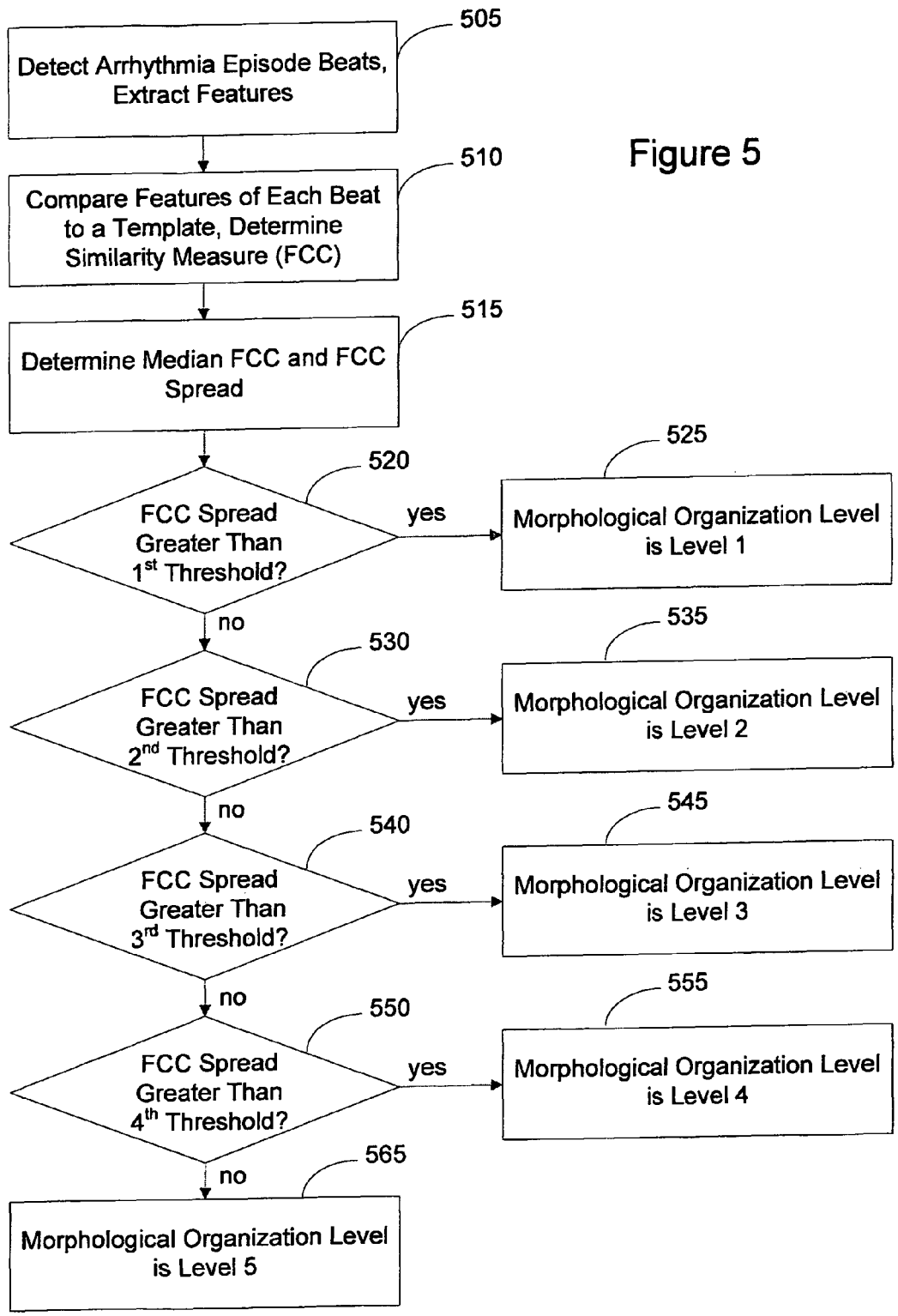
FIG. 5 is a flowchart illustrating a process of determining the morphological organization level based on the spreadness of the beat features in accordance with embodiments of the invention.

In another example, the morphological regularity of episode beats may be determined by calculating a spreadness of the beat features from a template. The morphological organization level may be determined based on the spreadness of the beat features as illustrated in the flowchart of FIG. 5. The arrhythmia beats are detected and features of the beats are extracted 505 for comparison to a template. In this example, each beat is compared 510 to the template by calculating a feature correlation coefficient (FCC), although other measures of similarity may be used. The median FCC and the FCC spread are determined 515. The median FCC is the median value of the FCCs for all the beats of the arrhythmia episode used for morphological organization level determination. The FCC spread is the number of FCC values that are within a window centered at the median FCC.

Morphological organization level is determined based on a FCC spread threshold associated with each organization level. The FCC spread is compared 520, 530, 540, 550 to the threshold for each morphological organization level. If the FCC spread is consistent with the threshold for a particular morphological organization level, then the arrhythmia episode is classified 525, 535, 545, 555, 565 as having that morphological organization level. Highly organized arrhythmias corresponding in this example to a morphological organization level of 1, have the highest FCC spread corresponding to the highest number of FCC values within the window centered at the median FCC. The most disorganized arrhythmias, corresponding in this example to morphological organization level 5, have the lowest FCC corresponding to the least number of beats having FCC values within the window centered at the median FCC. Methods and systems for determining morphological regularity such as those described herein are further discussed in commonly owned U.S. Pat. No. 7,430,446, which is incorporated herein by reference.

In some embodiments, the morphological organization level of the arrhythmia may be based on determination of the complexity of the cardiac electrogram signal of the arrhythmia episode. The complexity of the electrogram may be quantified using sample entropy. Sample entropy is a statistical measure of the irregularity of complexity of a signal or system. A smaller sample entropy indicates a lower degree of irregularity or a higher degree of complexity. A larger sample entropy indicates a higher degree of complexity Examples of using sample entropy in physiological signal analysis, are discussed in Lake et al., *Am. J. Physiol. Regul. Integr. Comp. Physiol.*, 283: R789-97 (2002) and Richman et al., *Am. J. Physiol. Heart Circ. Physiol.*, 278: H2039-49 (2000).

Sample entropy may be computed for a signal recorded over a certain length of time to indicate the degree of irregularity of the degree of complexity of that signal. The signal is digitized into a sequence of n samples: $u(1), u(2), u(3), \ldots u(n)$. In one embodiment, the sequence is a sequence of scalars, i.e., each sample is a scalar. In another embodiment, the sequence is a sequence of vectors, i.e., each sample $u(i)$ is a vector of p scalars: $u(i)=[u_1(i), u_2(i), u_3(i), \ldots u_p(i)]$. The following discussion of sample entropy applies when the n samples are a set of scalars or a set of vectors.

The sequence of samples is divided into $n-m+1$ signal segments each including m samples and denoted $x_m(i)=[u(i), u(i+1), \ldots u(i+m^{-1})]$, where $1 \leq i \leq (n-m+1)$, and m is a number smaller than n and represents the length of each signal segment. A vector matching score $D_m(i,j)$ between $x_m(j)$ and $x_m(i)$, where $j \neq i$, which is a measure of similarity between the two signal segments, is given as follows:

$$D_m(i, j) = \begin{cases} 1, & L[x_m(j), x_m(i)] \leq r; \\ 0, & \text{otherwise,} \end{cases} \quad (1)$$

where L is the maximum difference between corresponding components of signal segments $x_m(j)$ and $x_m(i)$ given by:

$$L[x_m(j), x_m(i)] = \max_{k=0 \approx m-1} \{L[u(j+k), u(i+k)]\}, \quad (2)$$

and r is a threshold. In one embodiment, the parameters n, m, and r are each empirically determined. L indicates the similarity between signal segments $x_m(j)$ and $x_m(i)$. In one embodiment, the sample entropy is given by:

$$SampEn(m,n,r) = -\ln [\Gamma(m,n,r)], \quad (3)$$

where:

$$\Gamma(m, n, r) = \frac{\sum_{i=1}^{n-m-1} \sum_{j=i+1}^{n-m} D_{m+1}(i, j)}{\sum_{i=1}^{n-m-1} \sum_{j=i+1}^{n-m} D_m(i, j)} \in [0, 1]. \quad (4)$$

In one embodiment, SampEn is a parameter used to indicate the degree of morphological irregularity or complexity of the signal recorded over the certain length of time. SampEn is compared to a plurality of predetermined entropy thresholds $\theta_1, \theta_2, \theta_3, \ldots$ corresponding respectively to morphological organization levels $1, 2, 3, \ldots$ to determine the morphological organization level of the arrhythmia episode. In another embodiment, $\Gamma$ is a parameter used to indicate the degree of morphological irregularity or complexity of the signal recorded over time. $\Gamma$ is compared to a plurality of predetermined entropy thresholds $\gamma_1, \gamma_2, \gamma_3, \ldots$ corresponding respectively to morphological organization levels $1, 2, 3, \ldots$ to determine the morphological organization level of the arrhythmia episode.

In some implementations, the morphological organization level of the arrhythmia episode is determined based on using SampEn or $\Gamma$ for analysis of the irregularity of the electrogram signal based on cycle length. In other implementations, the morphological organization level of the arrhythmia episode is based on using SampEn or $\Gamma$ for analysis of the morphological complexity of the electrogram. In further implementations, the morphological organization level of the arrhythmia episode is determined based on both analysis of the entropy associated with the cycle length irregularity of the electrogram signal and analysis of the entropy associated with the morphological complexity of the electrogram signal. The use of entropy measures to analyze the morphological complexity of the electrogram signal by cycle length irregularities and/or morphological complexity is further described in commonly owned U.S. Pat. No. 7,480,529, which is incorporated herein by reference.

In one embodiment, morphological organization can be estimated by using hemodynamic sensor signals. Examples of these sensors include impedance sensors, pressure sensors, heart sound sensors, oxygen saturation sensors, activity sensors, and others. When hemodynamic sensors are used, the morphological organization determination may not necessarily be based on the continuous recording of the sensor signal. The morphological organization may be determined from parameters extracted from the signal morphology of the hemodynamic sensor signals which are able to characterize and quantify the hemodynamic compromise during tachyarrhythmias. For example, if a pressure sensor is used, the parameters such as the mean value (computed over a designated period of time), the variation of the pressure, the time derivative (dP/dt) of the pressure, and/or other features can be extracted or computed from the pressure sensor signal. Values of these features are then compared to their respective thresholds, which may be determined during the normal sinus rhythm, to determine the morphological organization level of the arrhythmia.

In one embodiment, hemodynamic sensor signals may be used in conjunction with cardiac electrical signal sensors. When hemodynamic sensors are used together with the cardiac electrical activity sensors such as the electrocardiography (ECG) or electrograms (EGM), the morphology organization can be first determined using the ECG or EGM only, using the methods such as the entropy or other morphology regularity measures. After the initial morphological organization is determined from the ECG or EGM, one or more hemodynamic senor signals may be used to determine the hemodynamic stability. Based on the stability determined using one or more hemodynamic sensor signals, the initial morphological organization level previously determined from the ECG/EGM only may be adjusted. Examples of the use of hemodynamic sensors in connection with detection and treatment of cardiac arrhythmias are described in the following U.S. patents which are incorporated herein by reference: U.S. Pat. No. 5,330,505 (describes the use of cardiac electrical sensors and/or hemodynamic sensors used to adjust cardiac therapy) U.S. Pat. No. 4,865,036 (describes the use of pre-ejection period as measured by an intracardiac impedance sensor to confirm tachyarrhythmia), U.S. Pat. No. 5,176,137, (describes diagnosis of unstable tachyarrhythmia based in part on oxygen saturation level), and U.S. Pat. No. 5,554,177, (describes the use of heart sound sensor to adjust cardiac therapy. The techniques of the incorporated by reference patents may be used in conjunction with the methods and systems for automatic multi-level therapy based on morphological organization of arrhythmia as exemplified by the embodiments of the invention presented herein.

Embodiments of the present system illustrated herein are generally described as being implemented in a patient internal CRM device, which may operate to detect and deliver multi-level therapy for treatment of tachyarrhythmia. Various types of single and multiple chamber CRM devices may be used to implement a number of pacing therapies as are known in the art, in addition to delivering the tachyarrhythmia therapy.

It is understood that configurations, features, and combination of features described in the present disclosure can be implemented in a wide range of implantable or external medical devices, and that such embodiments and features are not limited to the particular devices described herein. The systems and methods described herein may be implemented in a wide variety of implantable or external diagnostic and/or therapeutic cardiac devices such as defibrillators, cardioverters, pacemakers, cardiac monitors, and resynchronizers, for example.

Although the present system is described in conjunction with an implantable cardiac defibrillator having a microprocessor-based architecture, it will be understood that the implantable cardiac defibrillator (or other device) may be implemented using any logic-based integrated circuit architecture, if desired.

In one embodiment, the CRM device is an implantable cardioverter/defibrillator configured as a single chamber device that operates to process cardiac signals and to deliver multi-level therapy based on morphological organization of the electrogram signals according to a methodology in accordance with the principles of the present invention. In another embodiment, the CRM device is an implantable cardioverter/defibrillator that is configured as a dual chamber device. In yet another embodiment, the CRM device is an implantable cardioverter/defibrillator configured to sense and/or provide electrical stimulation to multiple heart chambers, for example, both ventricles of the heart, as in a resynchronizer used to treat congestive heart failure (CHF).

Figure 6:
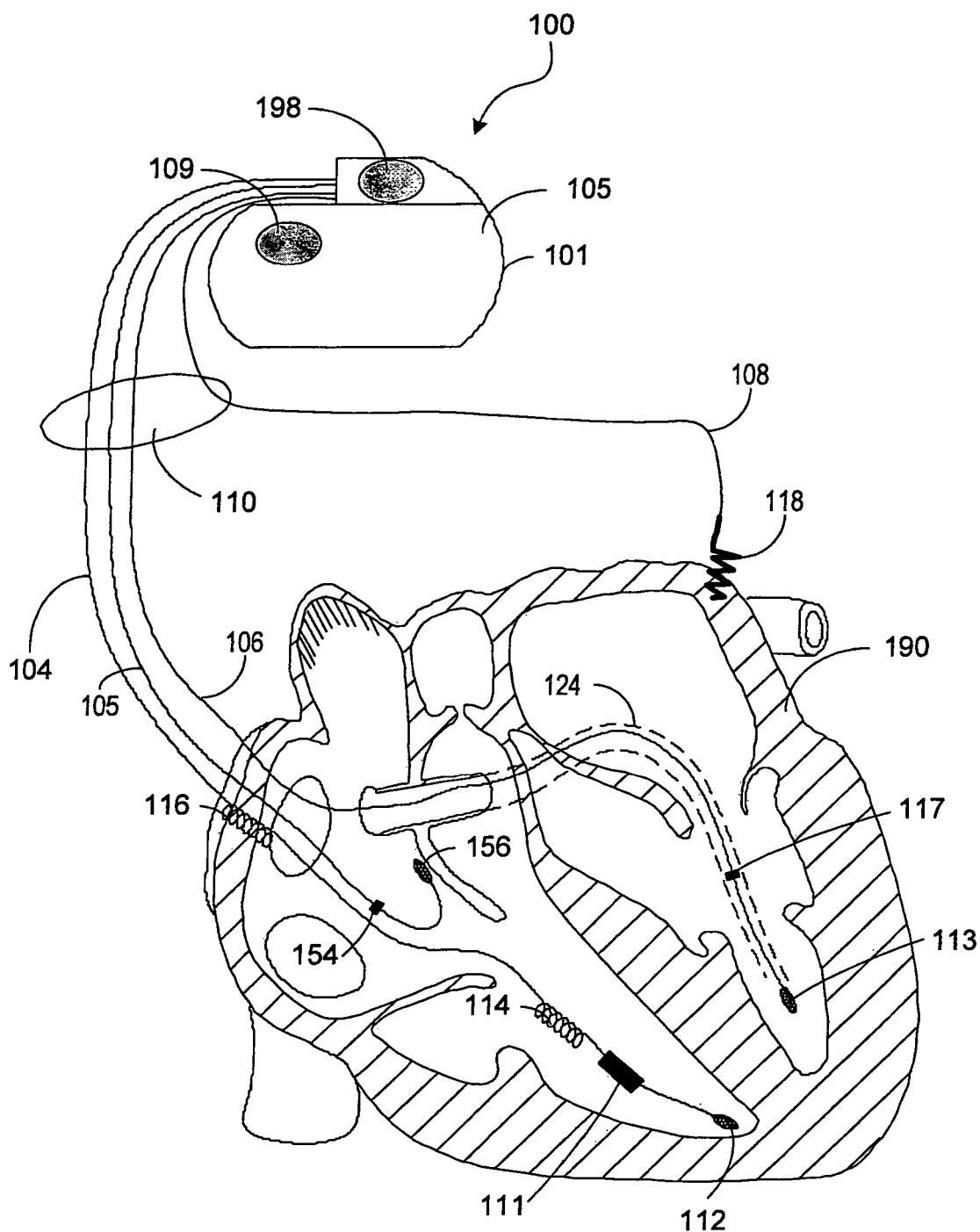
FIG. 6 is a partial view of one embodiment of an implantable medical device that may be used to deliver multi-level therapy based on morphological organization level of the arrhythmia in accordance with embodiments of the invention.

Referring now to FIG. 6 of the drawings, there is shown one embodiment of a cardiac rhythm management system that may be used to implement tachyarrhythmia therapy selection methods of the present invention. The cardiac rhythm management system in FIG. 6 includes a pulse generator (PG) 100 electrically and physically coupled to a lead system 110. The housing and/or header of the PG 100 may incorporate one or more electrodes 108, 109 used to provide electrical stimulation energy to the heart and to sense cardiac electrical activity. The PG 100 may utilize all or a portion of the PG housing as a can electrode 109. The PG 100 may include an indifferent electrode 198 positioned, for example, on the header or the housing of the PG 100. If the PG 100 includes both a can electrode 109 and an indifferent electrode 198, the electrodes 198, 109 typically are electrically isolated from each other.

The lead system 110 is used to detect electric cardiac signals produced by the heart 190 and to provide electrical energy to the heart 190 under certain predetermined conditions to treat cardiac arrhythmias. The lead system 110 may include one or more electrodes used for pacing, sensing, and/or cardioversion/defibrillation. In the embodiment shown in FIG. 6, the lead system 110 includes an intracardiac right ventricular (RV) lead system 104, an intracardiac right atrial (RA) lead system 105, an intracardiac left ventricular (LV) lead system 106, and an extracardiac left atrial (LA) lead system 108. The lead system 110 of FIG. 6 illustrates one embodiment that may be used in connection with the multi level tachyarrhythmia therapy methodologies described herein. Other leads and/or electrodes may additionally or alternatively be used.

The lead system 110 may include intracardiac leads 104, 105, 106 implanted in a human body with portions of the intracardiac leads 104, 105, 106 inserted into a heart 190. The intracardiac leads 104, 105, 106 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 6, the lead system 110 may include one or more extracardiac leads 108 having electrodes, e.g., epicardial electrodes, positioned at locations outside the heart for sensing and/or pacing one or more heart chambers.

The right ventricular lead system 104 illustrated in FIG. 6 includes an SVC-coil 116, an RV-coil 114, an RV-ring electrode 111, and an RV-tip electrode 112. The right ventricular lead system 104 extends through the right atrium 120 and into the right ventricle 119. In particular, the RV-tip electrode 112, RV-ring electrode 111, and RV-coil electrode 114 are positioned at appropriate locations within the right ventricle for sensing and delivering electrical stimulation pulses to the heart. The SVC-coil 116 is positioned at an appropriate location within the right atrium chamber of the heart 190 or a major vein leading to the right atrial chamber of the heart 190.

In one configuration, the RV-tip electrode 112 referenced to the can electrode 109 may be used to implement unipolar pacing and/or sensing in the right ventricle. Bipolar pacing and/or sensing in the right ventricle may be implemented using the RV-tip 112 and RV-ring 111 electrodes. The RV-ring 111 electrode may optionally be omitted, and bipolar pacing and/or sensing may be accomplished using the RV-tip electrode 112 and the RV-coil 114, for example. Sensing in the RV may involve the tip-to-ring vector and the RV-coil to SVC-coil or the RV-coil to SVC coil electrically tied to the can vector. The right ventricular lead system 104 may be configured as an integrated bipolar pace/shock lead. The RV-coil 114 and the SVC-coil 116 are defibrillation electrodes.

The left ventricular lead 106 includes an LV distal electrode 113 and an LV proximal electrode 117 located at appropriate locations in or about the left ventricle for pacing and/or sensing the left ventricle. The left ventricular lead 106 may be guided into the right atrium of the heart via the superior vena cava. From the right atrium, the left ventricular lead 106 may be deployed into the coronary sinus ostium, the opening of the coronary sinus. The lead 106 may be guided through the coronary sinus to a coronary vein 124 of the left ventricle. This vein is used as an access pathway for leads to reach the surfaces of the left ventricle that are not directly accessible from the right side of the heart. Lead placement for the left ventricular lead 106 may be achieved via subclavian vein access and a preformed guiding catheter for insertion of the LV electrodes 113, 117 adjacent to the left ventricle.

Unipolar pacing and/or sensing in the left ventricle may be implemented, for example, using the LV distal electrode 113 referenced to the can electrode 109. The LV distal electrode 113 and the LV proximal electrode 117 may be used together as bipolar sense and/or pace electrodes for the left ventricle. The left ventricular lead 106 and the right ventricular lead 104, in conjunction with the PG 100, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 105 includes a RA-tip electrode 156 and an RA-ring electrode 154 positioned at appropriate locations in the right atrium for sensing and pacing the right atrium. In one configuration, the RA-tip 156 referenced to the can electrode 109, for example, may be used to provide unipolar pacing and/or sensing in the right atrium 120. In another configuration, the RA-tip electrode 156 and the RA-ring electrode 154 may be used to effect bipolar pacing and/or sensing.

FIG. 6 illustrates one embodiment of a left atrial lead system 108. In this example, the left atrial lead 108 is implemented as an extracardiac lead with an LA distal electrode 118 positioned at an appropriate location outside the heart 190 for sensing and pacing the left atrium. Unipolar pacing and/or sensing of the left atrium may be accomplished, for example, using the LA distal electrode 118 to the can 109 pacing vector. The left atrial lead 108 may be provided with additional electrodes used to implement bipolar pacing and/or sensing of the left atrium.

Figure 7:
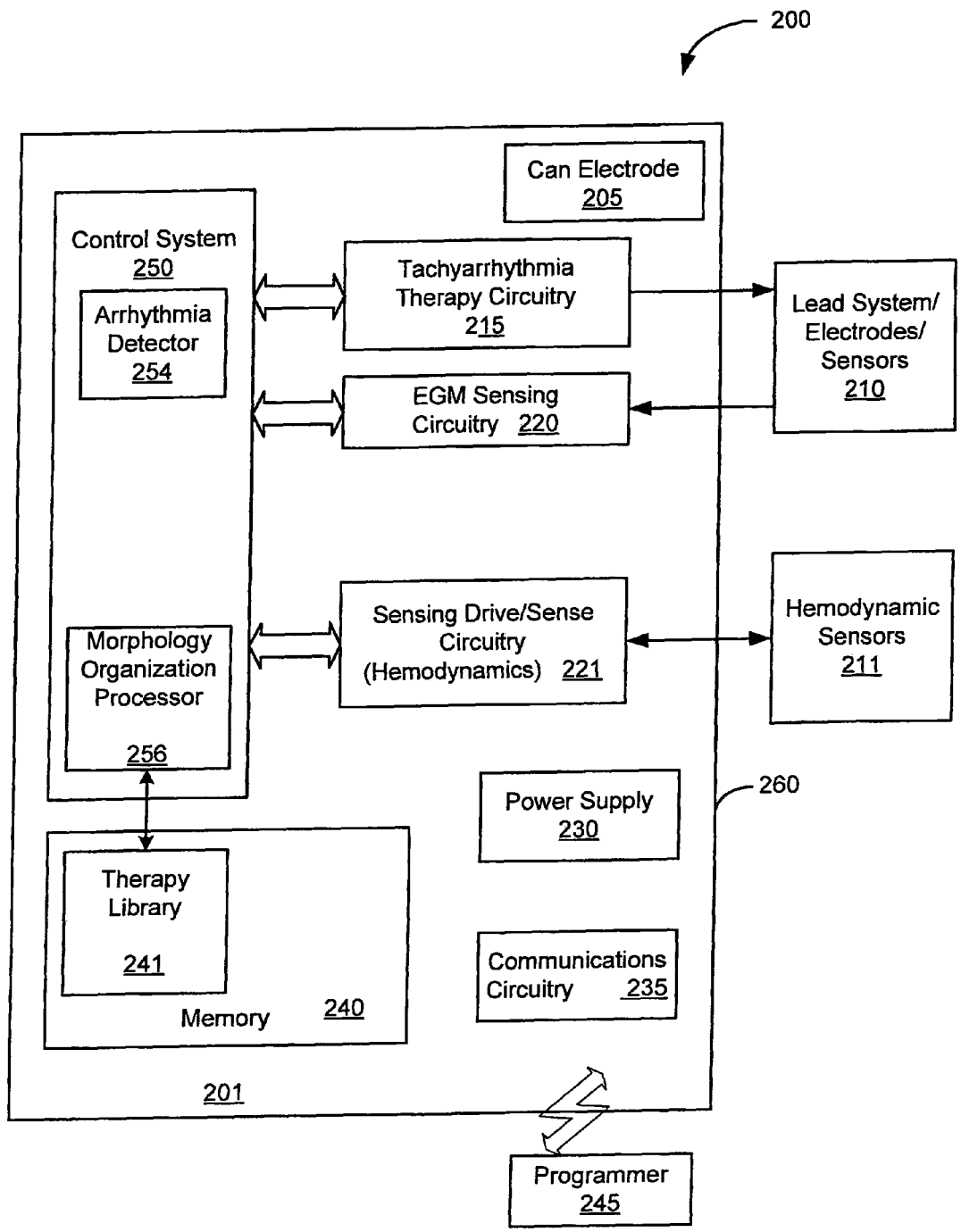
FIG. 7 is a block diagram illustrating functional components of an implantable medical device that may be used to deliver multi-level therapy based on morphological organization level of the arrhythmia in accordance with embodiments of the present invention.

Referring now to FIG. 7, there is shown a block diagram of an embodiment of a CRM device 200 employing a PG 260 suitable for implementing multi-level tachyarrhythmia therapy methodologies of the present invention. FIG. 7 shows the CRM device 200 divided into functional blocks. There exist many possible configurations in which these functional blocks can be arranged. The example depicted in FIG. 7 is one possible functional arrangement. The CRM device 200 includes circuitry for receiving cardiac signals from a heart and delivering electrical energy in the form of pace pulses or cardioversion/defibrillation pulses to the heart.

A cardiac lead system 210 may be implanted so that cardiac electrodes are electrically coupled to the heart tissue as described above in connection with FIG. 6. The cardiac electrodes of the lead system 210 sense cardiac signals associated with electrical activity of the heart. The sensed cardiac signals may be transmitted to a PG 260 through the lead system 210. The cardiac electrodes and lead system 210 may be used to deliver electrical stimulation generated by the PG 260 to the heart to mitigate various cardiac arrhythmias. The PG 260, in combination with the cardiac electrodes and lead system 210, may detect cardiac signals and deliver therapeutic electrical stimulation to any of the left and right ventricles and left and right atria, for example. For example, the PG 260 may deliver ATP, cardioversion, and/or defibrillation shocks to the heart through the lead system 210 in accordance with a multi-level tachyarrhythmia therapy of the present invention. A can electrode 205 coupled to a housing of the PG 260 may additionally be used to sense cardiac signals and deliver electrical stimulation to the heart.

In one embodiment, PG circuitry 201 is encased in a hermetically sealed housing suitable for implanting in a human body. Power is supplied by an electrochemical battery 230 that is housed within the PG 260. In one embodiment, the PG circuitry 201 is a programmable microprocessor-based system, including a control system 250, EGM sensing circuit 220 and a tachyarrhythmia therapy circuit 215, which may include pacing and shock therapy components. The PG circuitry 201 may also include a memory 240. The memory 240 may be used to store a therapy library 241 that includes associations between morphological organization level of a cardiac signal of a type of arrhythmia and therapies to treat arrhythmias. The memory 240 may be used to store parameters of the therapy and therapy components, and other parameters and/or data. The parameters and data stored in the memory 240 may be used on-board for various purposes and/or transmitted via telemetry to an external programmer unit 245 or other patient-external device, as desired.

In one embodiment, the PG circuitry 201 includes drive/sense circuitry 221 for the operation of one or more hemodynamic sensors 211. The signals produced by the sensor circuitry 211, 221 may be used to determine morphological organization level of the arrhythmia as previously described.

The control system 250 may used to control various subsystems of the PG 260, including the tachyarrhythmia therapy circuit 215, the electrogram sensing circuitry 220. The control system 250 may also include template circuitry for providing or processing one or more templates used in determination of the morphological organization of the electrogram according to embodiments of the invention.

Communications circuitry 235 allows the PG 260 to communicate with an external programmer unit 245 and/or other patient-external system(s). In one embodiment, the communications circuitry 235 and the programmer unit 245 use a wire loop antenna and a radio frequency telemetric link to receive and transmit signals and data between the programmer 245 and communications circuitry 235. In this manner, programming commands may be transferred to the PG 260 from the programmer 245 during and after implant. In addition, stored cardiac data may be transferred to the programmer unit 245 from the PG 260, for example.

Sensing circuitry 220 detects cardiac signals sensed at the cardiac electrodes 210. The sensing circuitry may include, for example, amplifiers, filters, A/D converters and other signal processing circuitry. Cardiac signals processed by the sensing circuitry may be communicated the control system 250, to the arrhythmia detector 254, and to the morphological organization processor (MOP) 256.

The arrhythmia detector 254 detects the presence of an arrhythmia, for example, by evaluating the rate and/or morphology of the electrogram signal. The MOP 256 performs various processes associated with determination of the morphological organization level of an arrhythmia episode. For example, the MOP 256 may use perform processes identified in the flowcharts of FIGS. 3, 4A, 4B, and 5. The MOP 256 may include implementations in hardware, software, and/or firmware.

The MOP 256 analyzes the signals from the electrogram sensing circuitry and/or the sensor circuitry to determine the morphological organization level of the detected arrhythmia episode. For example, the MOP 256 may evaluate the cardiac electrogram signal to determine the morphological regularity of the signal. The MOP 256 may alternatively or additionally analyze the cardiac electrogram signal to determine the entropy, e.g., irregularity and/or complexity, of the signal. Further, the MOP 256 may alternatively or additionally analyze signals derived from one or more hemodynamic sensors 211 to determine the hemodynamic stability of the arrhythmia episode. The MOP 256 determines the morphological organization level of the arrhythmia based on analysis of the electrogram and/or sensor signals.

Based on the morphological organization level of the arrhythmia episode, the MOP 256 accesses the therapy library 241 to identify a therapy associated with the morphological organization level of the arrhythmia. The tachyarrhythmia therapy circuit 215 controls delivery of the identified therapy. The MOP 256 may initialize and/or modify the therapy parameters and/or mapping associations between the morphological organization levels and therapies. For example, the MOP 256 may modify the morphological organization level to therapy associations and/or therapy parameters based on the success or failure of the delivered therapy as previously described. The new parameters and/or associations are stored in the therapy library 241.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for delivering cardiac therapy, comprising:
   detecting an arrhythmia episode;
   using a plurality of heartbeats in the detected episode to determine a parameter value that is indicative of a morphological organization of the episode;
   associating a plurality of morphological organization levels, respectively, with parameter values that are different from one another;
   classifying the detected arrhythmia episode into one of a plurality of morphological organization levels based on the determined parameter value, the plurality of morphological organization levels including at least a first, second, and third morphological organization level;
   associating the first, second, and third morphological organization levels with respective first, second, and third distinct cardiac therapy schemes, each of the cardiac therapy schemes including at least one cardiac therapy component to treat the detected arrhythmia; and
   delivering a selected cardiac therapy component that is associated with the morphological organization level of the detected arrhythmia episode.

2. The method of claim 1, wherein the first cardiac therapy scheme includes a first cardiac therapy component but not a second cardiac therapy component, and the second cardiac therapy scheme includes both the first and second cardiac therapy components.

3. The method of claim 2, wherein the first cardiac therapy component comprises a cardioversion therapy, and the second cardiac therapy component comprises a first anti-tachyarrhythmia pacing (ATP) therapy.

4. The method of claim 2, wherein the third cardiac therapy scheme includes the first cardiac therapy component, the second cardiac therapy component, and a third cardiac therapy component, the third cardiac therapy component not being included in either the first or second cardiac therapy schemes.

5. The method of claim 4, wherein the first cardiac therapy component comprises a cardioversion therapy, and the second cardiac therapy component comprises a first anti-tachyarrhythmia pacing (ATP) therapy, and the third cardiac therapy component comprises a second anti-tachyarrhythmia pacing (ATP) therapy.

6. The method of claim 1, wherein the plurality of morphological organization levels further includes a fourth morphological organization level.

7. The method of claim 6, wherein the fourth morphological organization level corresponds to a supraventricular tachyarrhythmia (SVT) and has associated therewith no cardiac therapy component to treat arrhythmia.

8. The method of claim 6, wherein the associating includes associating the first, second, third, and fourth morphological organization levels with respective first, second, third, and fourth distinct cardiac therapy schemes.

9. The method of claim 1, wherein at least two of the plurality of morphological organization levels correspond to monomorphic ventricular tachyarrhythmia (MVT).

10. The method of claim 9, wherein at least another two of the plurality of morphological organization levels correspond to polymorphic ventricular tachyarrhythmia (PVT).

11. The method of claim 1, wherein at least two of the plurality of morphological organization levels correspond to polymorphic ventricular tachyarrhythmia (PVT).

12. The method of claim 1, wherein determining the parameter value that is indicative of the morphological organization of the episode comprises determining the parameter value based on at least one of morphological regularity of a cardiac electrogram signal of the arrhythmia episode, entropy of the cardiac electrogram, and hemodynamic stability of the arrhythmia episode.

13. The method of claim 12, wherein determining the parameter value that is indicative of the morphological organization of the episode comprises determining the parameter value based on at least two of the morphological regularity, the entropy, and the hemodynamic stability.

14. The method of claim 1, wherein determining the parameter value that is indicative of the morphological organization of the episode comprises determining the parameter value based on rate irregularity of the arrhythmia episode.

15. The method of claim 1, wherein determining the parameter value that is indicative of the morphological organization of the episode comprises determining the parameter value based on morphological complexity of a cardiac electrogram signal of the arrhythmia episode.

16. The method of claim 1, wherein determining the parameter value that is indicative of the morphological organization of the episode comprises determining the parameter value based on hemodynamic stability of the arrhythmia episode.

17. The method of claim 1, further comprising:
   after the delivering, sensing for redetection of the arrhythmia.

18. The method of claim 17, wherein the sensing for redetection includes sensing for redetection more often for a more organized arrhythmia episode and less often for a less organized arrhythmia episode.

19. The method of claim 1, wherein the associating comprises statically associating the first, second, and third morphological organization levels with the respective first, second, and third distinct cardiac therapy schemes.

20. The method of claim 1, wherein the associating comprises dynamically associating the first, second, and third morphological organization levels with the respective first, second, and third distinct cardiac therapy schemes.

21. The method of claim 1, wherein the associating comprises associating the first, second, and third morphological organization levels with the respective first, second, and third distinct cardiac therapy schemes based on one or more of historical data, patient therapy tolerance, and physician input.

22. The method of claim 1, wherein the associating comprises dynamically changing the association of the first, second, and third morphological organization levels with the respective first, second, and third distinct cardiac therapy schemes based on efficacy of the cardiac therapy components.

23. The method of claim 1, further comprising:

determining an efficacy of the delivered cardiac therapy component; and modifying at least one of the first, second, or third cardiac therapy schemes based on an efficacy of the delivered cardiac therapy.

* * * * *